(12) United States Patent
Baccelli et al.

(10) Patent No.: US 10,034,761 B2
(45) Date of Patent: Jul. 31, 2018

(54) INTERSOMATIC IMPLANT AND TOOL FOR INSTALLING SUCH AN IMPLANT

(71) Applicant: Implanet, Martillac (FR)

(72) Inventors: Christian Baccelli, Saucats (FR); Regis Le Couedic, Bordeaux (FR)

(73) Assignee: Implanet, Societe Anonyme, Martillac (FR)

( * ) Notice: Subject to any disclaimer, the term of this patent is extended or adjusted under 35 U.S.C. 154(b) by 423 days.

(21) Appl. No.: 14/377,198

(22) PCT Filed: Feb. 7, 2013

(86) PCT No.: PCT/FR2013/050254
§ 371 (c)(1),
(2) Date: Aug. 7, 2014

(87) PCT Pub. No.: WO2013/117861
PCT Pub. Date: Aug. 15, 2013

(65) Prior Publication Data
US 2015/0012099 A1    Jan. 8, 2015

(30) Foreign Application Priority Data

Feb. 8, 2012    (FR) .................................... 12 00385

(51) Int. Cl.
*A61F 2/44* (2006.01)
*A61F 2/46* (2006.01)
*A61F 2/30* (2006.01)

(52) U.S. Cl.
CPC ............ *A61F 2/442* (2013.01); *A61F 2/4465* (2013.01); *A61F 2/4601* (2013.01);
(Continued)

(58) Field of Classification Search
CPC ............................. A61F 2/4465; A61F 2/4611
(Continued)

(56) References Cited

U.S. PATENT DOCUMENTS

| 8,956,414 B2* | 2/2015 | Asaad | A61F 2/4465 |
|---|---|---|---|
| | | | 606/99 |
| 2005/0125062 A1* | 6/2005 | Biedermann | A61F 2/442 |
| | | | 623/17.11 |

(Continued)

FOREIGN PATENT DOCUMENTS

| WO | 2009/040840 A1 | 4/2009 |
|---|---|---|
| WO | 2011/056172 A1 | 5/2011 |

OTHER PUBLICATIONS

International Search Report of PCT/FR2013/050254 dated May 29, 2013.

*Primary Examiner* — David Bates
(74) *Attorney, Agent, or Firm* — Banner & Witcoff, Ltd.

(57) ABSTRACT

The present invention concerns an intersomatic implant (2) comprising a body (4) suitable for being inserted between two vertebrae (1) to space them a predetermined distance apart, the body (4) being provided on either side, respectively, with a contact surface (5, 5') with the corresponding vertebrae (1). The body (4) is formed from an oblong part of predetermined thickness provided at a first so-called proximal end with a gripping cam (9) mounted movable in rotation relative to the part about an axis perpendicular to the two surfaces (5, 5'), between two predetermined angular positions. The contact surfaces (5, 5') are either parallel or substantially parallel to one another, and each contact surface (5, 5') of the body (4) with a corresponding vertebra (1) comprises a set of curved longitudinal protrusions (7, 7', 7") which decrease in height towards the distal ends thereof.

15 Claims, 3 Drawing Sheets

(52) U.S. Cl.
CPC ... *A61F 2/4611* (2013.01); *A61F 2002/30331* (2013.01); *A61F 2002/30364* (2013.01); *A61F 2002/30538* (2013.01); *A61F 2002/30542* (2013.01); *A61F 2002/30825* (2013.01); *A61F 2002/30828* (2013.01); *A61F 2250/0004* (2013.01); *A61F 2310/00023* (2013.01)

(58) Field of Classification Search
USPC .......................................... 623/17.11–17.16
See application file for complete search history.

(56) References Cited

U.S. PATENT DOCUMENTS

| | | | |
|---|---|---|---|
| 2006/0235426 A1* | 10/2006 | Lim | A61F 2/4465 606/99 |
| 2007/0282441 A1 | 12/2007 | Stream et al. | |
| 2008/0091211 A1* | 4/2008 | Gately | A61F 2/4465 606/99 |
| 2010/0094422 A1 | 4/2010 | Hansell et al. | |
| 2011/0276142 A1* | 11/2011 | Niemiec | A61F 2/442 623/17.16 |
| 2012/0165943 A1* | 6/2012 | Mangione | A61F 2/4465 623/17.16 |
| 2013/0023937 A1* | 1/2013 | Biedermann | A61F 2/4465 606/279 |
| 2013/0096685 A1* | 4/2013 | Ciupik | A61F 2/4465 623/17.16 |
| 2013/0268077 A1* | 10/2013 | You | A61F 2/4455 623/17.16 |
| 2015/0057753 A1* | 2/2015 | Barrus | A61F 2/4465 623/17.15 |

* cited by examiner

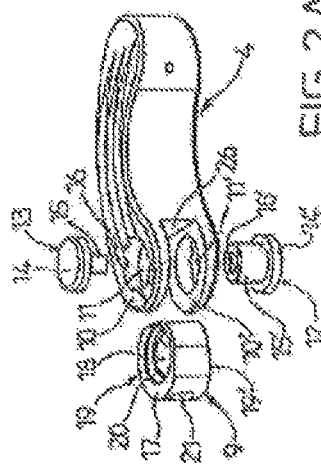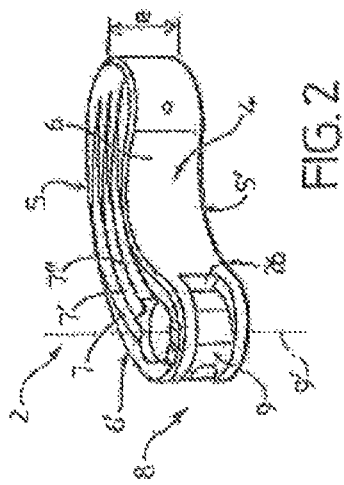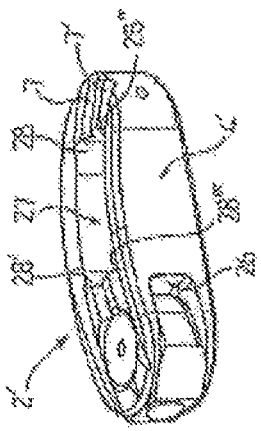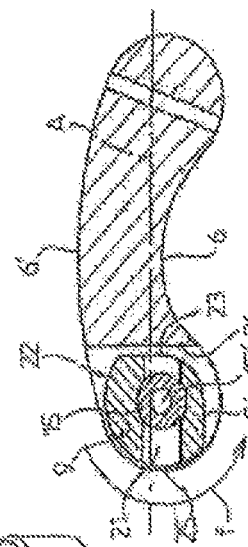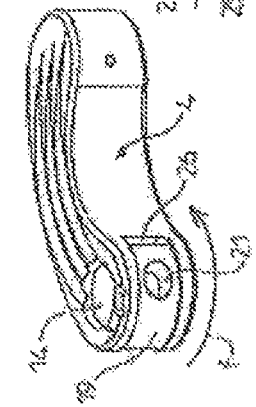

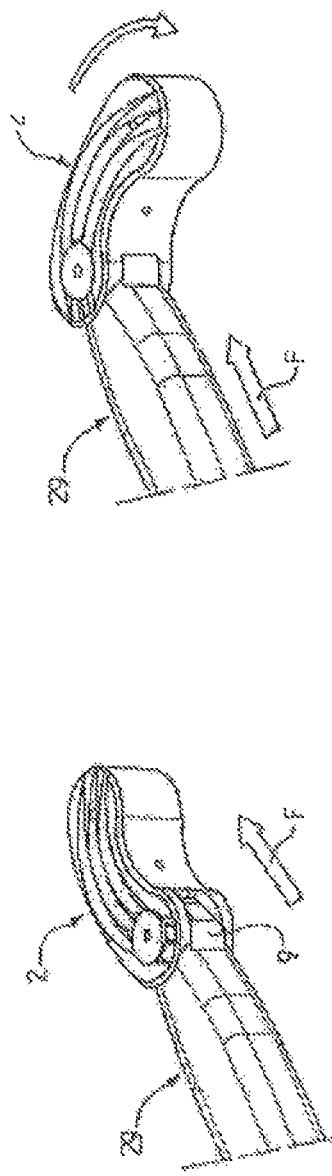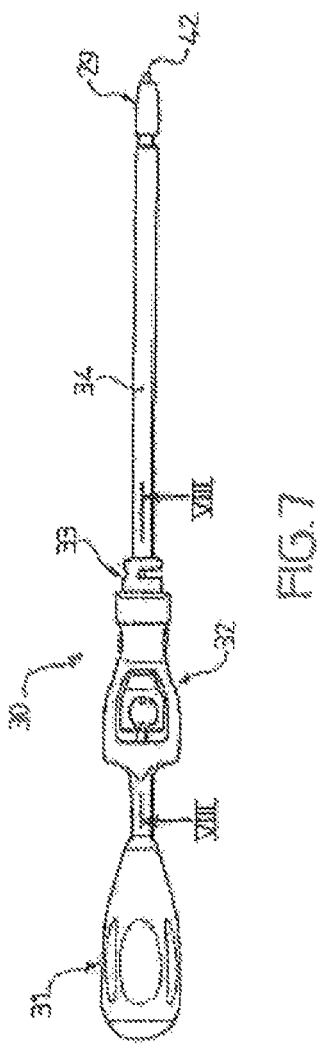

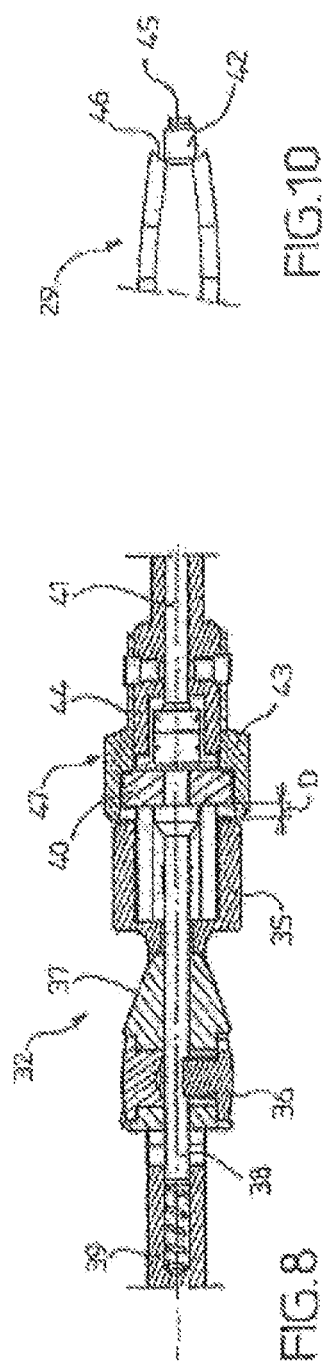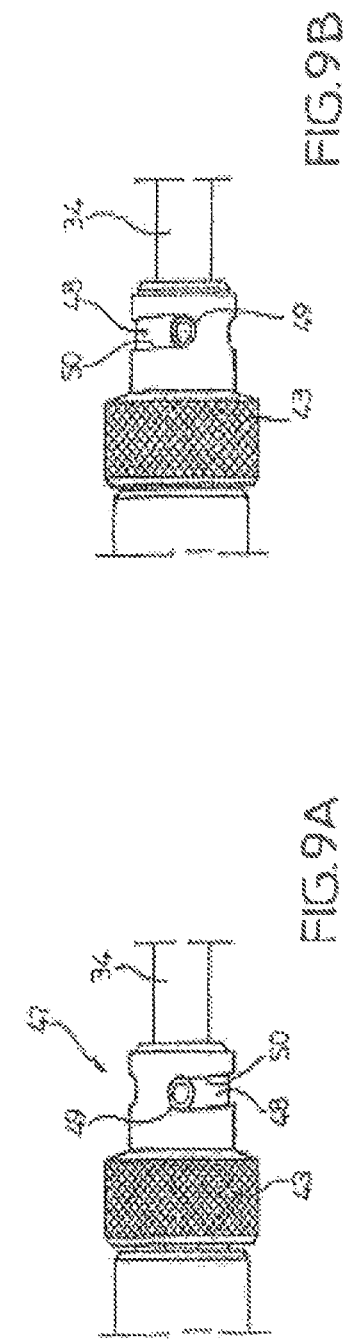

INTERSOMATIC IMPLANT AND TOOL FOR INSTALLING SUCH AN IMPLANT

The present invention relates to an intersomatic implant comprising a body that can be inserted between two vertebrae to part them by a determined distance and fit or not fit, a bone graft, the body being equipped on each side and respectively with a contact face for contact with, or situated on the same side as, a corresponding vertebra.

It also relates to a tool for installing such an implant.

The invention finds particularly significant, although not exclusive, application in the field of spinal surgery and notably in the field of intersomatic fusion.

Intersomatic implants intended to be inserted into the intervertebral space defined between two adjacent vertebrae are already known.

Such devices of parallelepiped overall shape have the disadvantage of requiring a large-sized incision, namely an incision of a size that is bigger than the size of the implant in the direction of insertion by enough that the surgeon, when using the traditional posterior route (on either side of the spinous), can introduce and fit said insert.

Implants comprising a pointed end for inserting them and teeth on the upper and lower faces in order to offer significant resistance to the expulsion of said implant once it has been installed, and do so in all directions, are also known.

Such devices nonetheless have the disadvantage of allowing only a small amount of control over the positioning of the implants, these implants being fitted through the combined action of a longitudinal thrust and the friction of the lateral walls of the implant against the periphery of the epiphysis. These devices are therefore neither flexible in terms of the positioning of the implant nor suited to patients who present with a damaged or weakened epiphysis.

The present invention seeks to supply an implant which is better suited than those known earlier to the requirements of everyday practice, notably insofar as it allows simple and automatic positioning of the implant, and does so with a small-sized incision.

In so doing, a significant proportion of the trauma associated with the intervention is avoided, and this in a more particularly fragile region close to the vertebral foramen (spinal cord and nerve roots).

To do so, it proceeds notably from the idea of fitting the implant via a transforamen route which is less aggressive to the nerve roots and to the dura mater than the posterior route.

To this end, the invention essentially proposes an intersomatic implant comprising a body that can be inserted between two vertebrae to part them by a determined distance and fit a bone graft, the body being equipped on each side and respectively with a contact face for contact with the corresponding vertebra, the body being formed of an oblong component of said determined thickness equipped at a first end, called the proximal end, with a gripping cam mounted with the ability to rotate with respect to the component about an axis perpendicular to the two faces, between two determined angular positions, characterized in that the contact faces are parallel or substantially parallel, and in that each contact face of the body for contact with a corresponding vertebra comprises a set of curved longitudinal reliefs substantially parallel to the lateral walls of a height that decreases toward their distal ends.

Advantageously, the contact faces are parallel over their entire surface (no tapering wedge).

Advantageously also, the contact faces are flat between the longitudinal reliefs, i.e. they form a smooth surface with no bumps or protrusions in addition to the curved longitudinal reliefs.

Such an arrangement will allow the body to be introduced at a certain angle, but limits its perceived size and then allow the body to be rotated to adopt a definitive position of parting the vertebrae by pressing on vertebrae on each side, with its full surface area.

It is thus possible for it to be introduced laterally, thereby limiting the size of the incision.

It is also possible to adapt the position of the implant in the vertebra to suite the pathology being treated and/or the physiological conditions of the patient (for example damaged epiphysis, etc.) notably by choosing the optimum distance between the implant and, on the one hand the vertebral foramen and, on the other hand the dura mater, something which becomes possible merely by guiding the upper and lower walls of the implant (which notably and incidentally are smooth).

In advantageous embodiments, recourse is also had to one and/or another of the following measures:

- the reliefs consist of ribs;
- the reliefs consist of grooves;
- the reliefs consist of an alternation of at least one rib and at least one groove;
- the reliefs extend over a distance comprised between ⅔ths and 9/10ths of the curved length of the implant and/or are shorter than ⅘ths of the length;
- the reliefs are separated from one another by plane or smooth curved surfaces, for example of the same width or substantially the same width to start with as the reliefs;
- the reliefs are in the form of ribs with a continuous upper ridge and/or which have decreasing triangular cross section;
- the decreasing triangular cross section decreases by a determined surface area, for example from 0.5 $mm^2$ to 0 $mm^2$;
- the component has two longitudinal lateral walls connecting the parallel or substantially parallel contact faces, of curved shape;
- the cross section of the component parallel to the contact faces (5, 5') is constant and in the shape of a kidney bean.
- the cam is formed of a substantially cylindrical ring pierced right through with a bore that is a slip fit on first pin secured to the component forming the axile perpendicular to the two faces;
- the ring has a lateral threaded hole pierced as far as the bore, for the passage of an instrument able to immobilize or free the cam angularly on the perpendicular axile with respect to the component of the body;
- the component at its proximal end has two parallel cheeks in the continuation of the contact faces open to the outside and between which the cam is inserted as a slip fit;
- the first pin is equipped on one side with a head that passes into a first cheek and on the other side collaborates with a second pin that is screwed onto the first pin through the opposite cheek;
- the cam has two flats for immobilizing it in each of its determined angular positions on the body;
- the body and the cam are made of titanium or of polymer.

The invention also proposes an insertion tool for installing an implant as described hereinabove.

To do this, proposes an insertion tool for inserting an implant as described hereinabove, characterized in that it comprises a shank provided with retractable gripping end piece that can be retracted with respect to the end of the shank, the surface of this end being of a shape that complements that of the proximal end of the implant, in that the gripping end piece is threaded so that it can be screwed into the threaded hole of the ring of the implant, and in that the tool comprises means for retracting the end piece inside the shank between a position in which it is screwed to the implant and a position in which it releases the implant.

Advantageously, the means for retraction comprise a cylindrical ring capable of turning and comprising a spiral guide slot for guiding a pin fixed to an axle secured to the retractable end.

In one advantageous embodiment, the retraction means comprise a spring designed to push the retractable end (in the rest position) outside the shank.

The invention will be better understood from reading the following description of some embodiments which are given hereinafter by way of nonlimiting examples.

The description refers to the accompanying drawings in which:

FIG. 1 is a vertebra viewed from above, on which an implant according to a first embodiment of the invention has been featured schematically.

FIG. 2 is a perspective view of the implant of FIG. 1, with the cam in a first position.

FIG. 2a is an exploded view of the implant of FIG. 2.

FIG. 3 is a perspective view of the implant of FIG. 2 with the cam in a second position.

FIG. 4 is a view in cross section of the implant of figure viewed from above.

FIG. 5 is a perspective view of another embodiment of the implant according to the invention, with an orifice for fitting a graft.

FIGS. 6A and 6B illustrate the fitting of the implant in the introduction position (FIG. 6A) and then while it is being rotated for definitive fitting (FIG. 6B).

FIG. 7 is a lateral view of a tool according to one embodiment of the invention.

FIG. 8 is a view in partial cross section on VIII-VIII of FIG. 7.

FIGS. 9A and 9B show an enlarged view of a retraction ring according to one embodiment of the tool according to the invention, before and after retraction.

FIG. 10 is a partial view of the end piece of the tool more specifically described.

FIG. 1 shows a vertebra viewed from above, on which an implant 2 is placed.

The invention can be used with all types of vertebrae, notably cervical, thoracic, lumber, or pelvic vertebrae.

Depending on the condition of the intervertebral disk 3 between the two vertebrae the implant is inserted into or next to the disk 3 in the direction of the arrow F.

FIG. 2 shows the implant 2 which takes the form of a body 4 in the form of a small plate of constant thickness having an oblong-shaped appearance, provided on each side and respectively with a contact face 5, 5' for contact with a corresponding vertebra, namely an upper contact face 5 and a lower contact face 5', which are parallel to one another.

More specifically, the body 4 has a constant longitudinal section parallel to the faces, for example in the shape of a kidney bean, defining curved lateral longitudinal walls 6, 6' perpendicular to the faces 5 and 5', the wall 6 having a smaller radius of curvature than the wall 6'.

This shape notably allows the implant 2 to pass around the gelatinous part (not depicted) of the intervertebral disk 3 by being anchored in the fibrous part of the disk 3 in order to avoid the proximity of the nerves of the spinal column.

At least one contact face 5, 5' comprises a set of longitudinal reliefs forming ribs or concave grooves, for example three curved ribs 7, 7', 7" substantially parallel to one another and to said curved lateral walls 6, 6'.

The reliefs, are, for example, equal to at least ⅗ths of the length of the body, in depth (for example in the case of grooves) or in projection (in the case of ribs) with respect to the surface, for example having a V-shaped profile.

In the embodiment more specifically described here, the grooves project and have a height that decreases overall toward the end intended to be the first to enter the space between the vertebrae (distal end).

The radii of curvature of the curved grooves 7 for example increase the further these grooves are from the center of the concavity.

The configuration of grooves 7, 7', 7" will, by the rubbing of the ribs against the surfaces of the vertebrae 1 and/or of the intervertebral disk 3, allow a natural rotation of the implant 2 encouraging it to position itself automatically.

According to the embodiment more particularly described, the two contact faces 5, 5' each comprise a set for example of three grooves, the sets being symmetric with one another about the median transverse plane of the body 4.

Thus, when the implant 2 is installed between two vertebrae, the upper face 5 is in contact with the lower face of the upper vertebra, and the lower face 5' of the implant is in contact with the upper face of the lower vertebra, said faces defining a plate of determined thickness e corresponding to the desired spacing distance and/or to the minimum distance between the two superposed vertebrae.

The thickness e is comprised for example between 6 mm and 18 mm.

The body 4 comprises at one (8) of its ends, a gripping cam 9 mounted with the ability to turn with respect to the body 4 about an axis 9' perpendicular to the two faces 5, 5', between two determined angular positions.

FIG. 2A shows the gripping cam 9 dismantled as well as the end 8 of the body 4 that is to accept the gripping cam 9.

More specifically, a recess formed by two parallel partially circular disk-shaped cheeks 10, 10' situated in the continuation of the contact faces 5, 5' is provided to accept the cam 9, which is inserted therein so as to be a slip fit with said cheeks.

Each cheek 10, 10' comprises a through-hole 11, 11' passing through its thickness, positioned more or less at its center, the holes facing one another and being intended respectively to accept the pins 12 and 13 with which they collaborate.

Each pin 12, 13 has a cylindrical head 14, 14' of a diameter slightly smaller than that the corresponding hole, 11, 11' so as to be able to be inset therein while remaining free to turn, and a cylindrical body 15, 15' secured to the corresponding head 14, 14'.

The body 15 is formed of a shank of a length shorter than that of the recess between the two cheeks and is designed to collaborate with the body 15' itself formed of a small cylinder hollowed by a bore 16' into which the shank 15 can fit.

After the fitting of the cam 9 which will be described more specifically hereinafter, the two pins 12, 13 are fixed together, for example by bonding or welding.

The gripping cam 9 is formed of a substantially cylindrical ring 17 of a diameter similar to that of the cheeks 10, 10' and of a height designed to allow it to pivot freely with a small amount of friction in the space defined between the cheeks 10, 10'.

The ring 17 is pierced right through with a bore 18 the internal surfaces of which are a slip fit against the external wall of the cylindrical body 15' thus forming an axle for rotation of the ring which is perpendicular to the two faces.

In one embodiment, the gripping cam 9 comprises, on at least one of its upper 19 and/or lower 19' faces, an external bore 20 of a diameter larger than that of the bore 18, able to form a shoulder designed to collaborate with the head 14, 14' of the corresponding pins 12, 13.

The gripping cam 9 moreover comprises a threaded lateral hole 21 pierced as far as the bore 18, for the passage of an instrument able to immobilize or free the rotation of the cam 9 angularly on the axle formed by the pins.

FIG. 3 shows the implant of FIG. 2 after the cam 9 has been turned (arrow f).

FIG. 4 is a view from above, in cross section, of the implant 2 showing the gripping cam 9 in the insertion position.

The axis of the lateral threaded hole 21 is then substantially parallel to the (approximative) proximal/distal axis A of the body 4 of the implant 2.

According to the more particularly described embodiment of the invention, the gripping cam 9 additionally has a lateral wall 22 provided with two immobilizing flats 23, 24 that make an angle α between them, and which are connected to one another by a rounded surface 25 tangential to said flats.

For preference, the angle α is comprised between 60° and 100°, and is for example 90°.

During rotation about the axle 9' of the pins 12, 13 of the gripping cam 9, each flat 23, 24, depending on the direction of rotation, will come into abutment with the flat internal part 26 of the body 4 of the implant, which for example is perpendicular or substantially perpendicular to the axis A.

The angle α thus defines the angular range of rotation of the cam 9 by abutment of one of the flats 23, 24 and then other.

FIG. 5 shows an implant 2' similar to that described previously and provided with a central recess 27 for a graft.

In the remainder of the description the same reference numerals have been used to denote elements that are identical or similar.

More specifically, the body 4' of the implant 2' comprises a central part of greater width provided with the recess 27, for example of rectangular cross section, passing right through the body.

The corners 28, 28', 28'', 28''' of this recess 27 are advantageously rounded, this recess being more or less centered on the body 4.

Once again, the surfaces 5, 5' comprise longitudinal and curved recessed reliefs 7, 7' forming grooves of increasing depth, increasing from the distal end to the proximal end, the grooves 7, 7' having a V-shaped profile and forming a point at the distal end.

The grooves 7, 7' have the same properties as those defined with reference to FIG. 2 and run from one end of the implant 2 to the other, being interrupted by the orifice 27 which for example is obtained by the removal of material.

The orifice 27 allows for the insertion of a graft, namely a piece of bone tissue that can be implanted into the human body.

Of course, the implant 2 may be made of any material that is biocompatible and preferably suitable for being implanted into the human body, for example titanium or decomposable polymer.

The introduction of an implant 2 according to one embodiment of the invention and the tool necessary for doing so will now be described.

FIGS. 6A and 6b first of all show an implant connected to the head 29 of an insertion tool 30 (see FIG. 7) at the start and the end of the operation respectively.

The tool 30 is of longilinear overall shape, likenable to a screwdriver. It is made up in its most proximal part of a gripping handle 31 followed by an immobilizing/release mechanism 32 for immobilizing/releasing the connection between the gripping cam 9 and the tool 30.

The latter also comprises a mechanism 33 for freeing the rotation of the gripping cam 9 via a shank cylinder 34 provided in its most distal part with the head 29 for connecting to the gripping cam 9.

The cylindrical shank 34, which is relatively long in size, for example between 15 and 25 cm long, notably allows the practitioner to work a sufficient distance away from the incision in order to avoid having to organize a passage for tools into the body of the patient and/or significant displacement of the organs that impede such passage, thus minimizing the surgical risks and the trauma to said organs. It also allows the implant 2 to be pushed into the disk 3 easily.

FIG. 8 is a schematic and more detailed view in cross section of the immobilizing/release mechanism 32.

The mechanism 32 that immobilizes/releases the connection of the gripping cam 9 is controlled by a screw 35 with a serrated head, designed as it turns to drive an immobilizing nut 37 mounted radially on a press shank 38.

The press shank 38 at its proximal end comprises precompressed spring 39 and is connected at its distal end to a circular stop 40 that is free to turn.

The stop 40 is contained within an internal space of dimensions suited to allowing it to more translationally, corresponding to a distance D of between 1 and 3 mm.

The stop 40 is connected on the other side to a shank 41 contained in the internal space defined by the shank 34 and opening to the distal end 29 of the tool 30 in the form of a threaded end 42 (FIG. 10).

The turning of the serrated head control screw 35 therefore causes the turning of the immobilizing nut 37 which itself turns the press shank 38 which transfers its movement to the stop 40 which turns the shank 41 thus allowing the tool 30 to be screwed to/unscrewed from the implant 2.

The mobile stop 40 is held in its longitudinal position by the press shank 38 against which the precompressed spring 39 presses.

A knurled ring 43 mounted on a thread translation cylinder 44 can be used to adjust the backpressure applied to the stop 40.

The translational movement of the stop 40 itself drives a translational movement of the shank 41 and therefore of the retractable end 42.

FIG. 10 schematically shows one embodiment of the connection tip 29.

The distal end of the tool 30 ends with an end of the support shank 34 from which there protrudes the retractable end 42 which itself ends in the screw thread 45 which can be screwed into the bore of the ring 17.

The shank 34 moreover at its end comprises a surface 46 with respect to which the retractable end 42 protrudes.

The surface 46 is concave, namely it is rounded toward the inside of the tool 30, in a shape that complements the proximal end of the implant 2.

In the position for immobilizing/locking the rotation of the retractable end, the latter is in a position which is retracted inside the cylinder, namely there is minimal protrusion of the retractable end 42 beyond the support cylinder 35.

In the position in which the rotation of the retractable end 42 is released/unlocked, the latter is in a position of maximum protrusion.

When the tool 30 is in the locked position the retractable end 42 held inside the ring 17 of the implant 2 keeps the latter in contact with the rounded surface 45 of complementary shape, the rounding of complementary shape preventing the implant 2 from turning.

During the transition between the immobilized and released positions, the implant 2 finds itself away from the rounded surface 46 of complementary shape which then no longer prevents the implant 2 from turning.

FIGS. 9A and 9B show a view of the control of the mechanism 47 for freeing the rotation of the implant 2 of the insertion tool 30 in the locked position and in the unlocked posit ion respectively.

Control is achieved via the knurled ring 43 on which a cylinder 45 comprising a radially projecting pin 49 is mounted.

The pin 49 is guided in a channel 50 which runs along the periphery of the cylinder 48, over less than one turn of the cylinder 48.

Thus, the pin 49 has two positions of abutment.

One is an immobilizing position when the knurled ring 43 is in the most proximal position it can occupy and the other is a release position when the knurled ring 43 is in its most distal position.

The fitting of an implant according to the more particularly described embodiment of the invention will now be described.

Having made an incision and/or removed material from the intervertebral disk 3, the medical practitioner, for example the surgeon, connects the distal end of the insertion tool 30 to the gripping cam 9.

This connection is achieved by screwing part of the end of the tool 30 into the screw thread of the lateral hole 21 of the ring 17.

Connection is performed over a shallow depth of the ring 17 such as that for example corresponding to four turns of the end of the tool 30 in the screw thread.

The small number of screw turns performed allows for easier disconnection of the tool 30 without entailing unwanted turning of the implant 2 in the direction in which the screwing action is being performed.

The surgeon then offers up to the incision the distal part at the opposite end from the gripping cam 9.

Insertion is made easier by the relatively small surface area of the inserted profile, namely the distal end of the implant 2, and by the practically zero height of the curved grooves 7, 7', 7' at this end.

The surgeon then pushes in a straight line collinear with the alignment of tool 30 and implant 2, in the direction of the arrow F (see FIGS. 6A and 6B).

With this push, friction between the implant 2 and ids surroundings increases, notably because of the grooves 7, 7', 7" and the fact that their height increases as the implant 2 moves forward into the disk 3.

The grooves 7, 7', 7" thus provide purchase in the insertion surroundings.

The radii of curvature of the grooves 7, 7', 7" then act as a guide rail and tend to cause the implant 2 to pivot, creating a turning force.

When the surgeon estimates that the implant 2 is suitable position, he makes the implant free to turn.

This release to provide freedom to turn is performed by making the gripping cam 9 free to turn.

Now that the cam 9 is free to turn in a certain angular range, under the effect of the pressure applied by the surgeon, the implant 2 then turns about a center that is the axis of the gripping cam 9.

The configuration of the gripping cam 9 and of its flats 23, 24 provides the angular range of freedom for the implant 2.

Under the combined effect of the oblong shape of the implant 2, of the grooves 7, 7', 7" and of the degree of freedom to turn of the cam 9, the implant 2 thus finds its position in the intervertebral disk 8.

It should then be noted that because of the automatic positioning of the implant 2 and because of its profile, the initial incision for inserting the implant can be smaller, thus implying lower surgical risks and less trauma to the patient.

The oblong profile itself reduces the area of insertion and therefore the resistance to insertion and optimizes penetration.

In embodiments comprising an internal lateral surface with a radius of curvature larger than that of the external lateral surface namely which are in the shape of a kidney bean, the bulbous nature of the ends of the implants creates resistance to lateral expulsion of the implant.

Despite the guidance performed by the reliefs and determining the resistance to said lateral expulsion, the invention provides not only excellent resistance to transverse influences, thanks to the reliefs, but experience shows that a very low degree of lateral expulsion/movement occurs.

As goes without saying and as is also evident from the aforegoing, the present invention is not restricted to the embodiments more specifically described. On the contrary, it encompasses all variants thereof.

The invention claimed is:

1. An intersomatic implant comprising a body that can be inserted between two vertebrae to part the two vertebrae by a determined distance and fit a bone graft therebetween, the body being equipped on each side and respectively with a contact face for contact with a corresponding vertebra, the body having lateral walls connecting the contact faces, the body being formed of an oblong component of the determined thickness equipped at a proximal end with a gripping cam mounted with the ability to rotate with respect to the oblong component about an axis perpendicular to the contact faces, between two determined angular positions, wherein the contact faces are parallel or substantially parallel, and each contact face of the body for contact with a corresponding vertebra comprises a set of curved longitudinal reliefs substantially parallel to the lateral walls and spaced apart from the lateral walls, the set of curved longitudinal reliefs being of a height that decreases starting from the proximal end and extending toward a distal end of the body, and wherein the set of curved longitudinal reliefs comprise ribs or grooves and/or an alternation of at least one rib and of at least one groove, the set of curved longitudinal reliefs being separated from one another by flat contact faces, each flat contact face extending from the proximal end to the distal end.

2. The intersomatic implant as claimed in claim 1, wherein the set of curved longitudinal reliefs comprise ribs.

3. The intersomatic implant as claimed in claim 2, wherein the ribs have a continuous upper ridge and a decreasing triangular cross section.

4. The intersomatic implant as claimed in claim 1, wherein the set of curved longitudinal reliefs comprise grooves.

5. The intersomatic implant as claimed in claim 1, wherein the set of curved longitudinal reliefs comprise an alternation of at least one rib and at least one groove.

6. The intersomatic implant as claimed in claim 1, wherein the oblong component has two longitudinal lateral walls of curved shape and connecting the parallel or substantially parallel contact faces.

7. The intersomatic implant as claimed in claim 1, wherein a cross section of the oblong component parallel to the contact faces is constant and in a shape of a kidney bean.

8. The intersomatic implant as claimed in claim 1, wherein the gripping cam is formed of a substantially cylindrical ring pierced through with a bore that is a slip fit on a first pin secured to the oblong component forming an axle perpendicular to the contact faces.

9. The intersomatic implant as claimed in claim 8, wherein the substantially cylindrical ring has a lateral threaded hole pierced as far as the bore, for passage of an instrument able to immobilize or free the gripping cam angularly on an axle perpendicular with respect to the oblong component of the body.

10. The intersomatic implant as claimed in claim 1, wherein the proximal end of the oblong component has two parallel cheeks, each cheek being an extension of one of the contact faces in a same plane as the one of the contact faces, the two parallel cheeks forming a recess open towards an outside direction of the body and between which the gripping cam is inserted as a slip fit.

11. The intersomatic implant as claimed in claim 10, wherein a first pin is equipped on one side with a head that passes into a first cheek and on a second side collaborates with a second pin that is screwed onto the first pin through an opposite cheek.

12. The intersomatic implant as claimed in claim 1, wherein the gripping cam has two flats for immobilizing the gripping cam in each of the determined angular positions on the body.

13. The intersomatic implant as claimed in claim 1, wherein the body and the gripping cam are made of titanium or of polymer.

14. The intersomatic implant as claimed in claim 1, wherein the set of curved longitudinal reliefs extend over a distance between $2/5$ths and $9/10$ths of a curved length of the intersomatic implant and/or are shorter than $4/5$ths of the curved length.

15. An implant system comprising:
 an intersomatic implant as claimed in claim 1; and
 a tool comprising:
  a support shank having one end; and
  a gripping shank having one end which projects from the one end of the support shank, the one end of the support shank defining a concave surface surrounding the end of the gripping shank and circumferentially facing toward an inside of the support shank, the concave surface being of a shape that complements the proximal end of the implant,
 wherein the one end of the gripping shank is threaded, and
 wherein the tool comprises a turning component for turning the gripping shank and a translational component for causing a translational movement of the gripping shank in the support shank.

* * * * *